(12) United States Patent
Tulchinsky et al.

(10) Patent No.: US 8,461,366 B2
(45) Date of Patent: Jun. 11, 2013

(54) SULFONATED ORGANOPHOSPHINE COMPOUNDS AND USE THEREOF IN HYDROFORMYLATION PROCESSES

(75) Inventors: Michael L. Tulchinsky, Midland, MI (US); Robert E. Hefner, Jr., Rosharon, TX (US)

(73) Assignee: Dow Global Technologies LLC, Midland, MI (US)

( * ) Notice: Subject to any disclaimer, the term of this patent is extended or adjusted under 35 U.S.C. 154(b) by 227 days.

(21) Appl. No.: 12/812,981

(22) PCT Filed: Jan. 9, 2009

(86) PCT No.: PCT/US2009/030556
§ 371 (c)(1),
(2), (4) Date: Aug. 2, 2010

(87) PCT Pub. No.: WO2009/091670
PCT Pub. Date: Jul. 23, 2009

(65) Prior Publication Data
US 2011/0054204 A1  Mar. 3, 2011

Related U.S. Application Data

(60) Provisional application No. 61/021,068, filed on Jan. 15, 2008.

(51) Int. Cl.
*C07C 303/00* (2006.01)
*C07F 17/02* (2006.01)
*C07F 15/00* (2006.01)

(52) U.S. Cl.
USPC .............................. 556/21; 556/136; 556/138

(58) Field of Classification Search
USPC ......................................................... 556/21
See application file for complete search history.

(56) References Cited

U.S. PATENT DOCUMENTS

| | | | |
|---|---|---|---|
| 2,900,393 A | 8/1959 | Broderick | |
| 3,527,809 A | 9/1970 | Pruett et al. | |
| 4,148,830 A | 4/1979 | Pruett et al. | |
| 4,247,486 A | 1/1981 | Brewester et al. | |
| 4,283,304 A | 8/1981 | Bryant et al. | |
| 4,483,802 A | 11/1984 | Gartner et al. | |
| 4,625,068 A | 11/1986 | Young | |
| 4,642,388 A | 2/1987 | Young | |
| 4,689,437 A | 8/1987 | Murray | |
| 4,716,138 A | 12/1987 | Murray | |
| 4,731,486 A | 3/1988 | Abatjoglou et al. | |
| 4,822,915 A | 4/1989 | Murray | |
| 5,180,854 A | 1/1993 | Abatjoglou et al. | |
| 5,382,701 A | 1/1995 | Suciu et al. | |
| 5,451,698 A | 9/1995 | Bahrmann et al. | |
| 5,663,426 A | 9/1997 | Albanese et al. | |
| 5,728,886 A | 3/1998 | Naumann et al. | |
| 5,760,286 A | 6/1998 | Brandvold | |
| 5,773,666 A | 6/1998 | Omatsu et al. | |
| 5,780,674 A | 7/1998 | Albanese et al. | |
| 5,925,785 A | 7/1999 | Stelzer et al. | |
| 5,929,289 A | 7/1999 | Abatjoglou et al. | |
| 5,932,772 A | 8/1999 | Argyropoulos et al. | |
| 5,952,530 A | 9/1999 | Argyropoulos et al. | |
| 6,103,908 A | 8/2000 | Bahrmann et al. | |
| 6,339,174 B1 | 1/2002 | Bogdanovic | |
| 6,610,881 B1 | 8/2003 | Riedel et al. | |
| 6,613,939 B2 | 9/2003 | Aouni et al. | |
| 6,864,387 B2 | 3/2005 | Riedel et al. | |
| 7,663,002 B2 * | 2/2010 | Peng et al. ..................... 568/454 |
| 2003/0204109 A1 | 10/2003 | Aouni et al. | |

FOREIGN PATENT DOCUMENTS

| | | |
|---|---|---|
| EP | 0350921 A1 | 1/1990 |
| EP | 1620387 A2 | 2/2006 |
| WO | WO 03042224 A2 * | 5/2003 |
| WO | WO-2004/094440 A2 | 11/2004 |
| WO | WO-2004/096744 | 11/2004 |
| WO | WO-2007035540 A2 | 3/2007 |

OTHER PUBLICATIONS

Abatjoglou et al, Organometallics, 1984, p. 923-926, vol. 3, American Chemical Society.
Arvidsson et al, Canadian Journal of Chemstry, 1998, p. 795-799, vol. 76, Canada.
Ashby, Journal of Organic Chemistry,1985, p. 3274-3283, vol. 50, American Chemical Society.
Bartik et al, Journal of Molecular Catalysis A: Chemical, 1995, p. 117-122, vol. 98, Elsevier Science BV.
Bartik et al, Organometallics, 1993, p. 164-170, vol. 12, American Chemical Society.
Doppiu et al, European Journal of Inorganic Chemistry, 2004, p. 2244-2252, Wiley-VCH.
Fleckenstein et al, Chemistry—A European Journal, 2007, p. 2701-2716, vol. 13, Wiley-VCH.
Frohning, Applied Homogeneous Catalysis with Organometallic Compounds, 2002, p. 29-103, vol. 1, Wiley-VCH, New York.
Furstner el al, Chemistry—A European Journal, 2000, p. 1847-1857, vol. 6, Wiley-VCH.
Jane et al, Journal of Organometallic Chemistry, 2000, p. 55-64, vol. 606, Elsevier Science SA.

(Continued)

*Primary Examiner* — Johann R Richter
*Assistant Examiner* — Kofi Adzamli

(57) ABSTRACT

A compound comprising a class of sulfonated triorganophosphine compounds of formula $R^1R^2P-R^3[-O-(CH_2)_n-(SO_3M)]_m$, wherein the $R^1$ and $R^2$ are selected individually from alkyl, aralkyl, and alicyclic groups, wherein $R^3$ represents a divalent or polyvalent alkylene or alicyclic radical that is bonded to the phosphorus atom and to one or more sulfonate substituents via an alkylether link, and further wherein $R^3$ does not contain any aryl moieties; n is an integer reflecting a number of methylene groups in the alkylether link; M represents a monovalent cation; and m is an integer representing a total number of sulfonated alkylether substituents. The compound is useful as a ligand in transition metal-ligand complex catalysts that are capable of catalyzing the hydroformylation of an olefinically-unsaturated compound with carbon monoxide and hydrogen to form one or more corresponding aldehyde products. The ligand is incapable of alkyaryl exchange, thereby leading to reduced ligand usage and improving ligand and rhodium recovery and recycling.

19 Claims, 1 Drawing Sheet

OTHER PUBLICATIONS

Kabalka et al, Tosylation of Alcohols, Journal of Organic Chemistry, 1986, p. 2386-2388, vol. 51, American Chemical Society.

Lynn et al, Journal of the American Chemical Society, 2000, p. 6601-6609, vol. 122, American Chemical Society.

Lysenko et al, Journal of Organometallic Chemistry, 2006, p. 5197-5203 vol. 69, Elsevier BV.

McNulty et al, Tetrahedron Letters, 2004, p. 407-409, vol. 45, Elsevier Ltd.

Mohr et al, Organometallics, 1996, p. 4317-4325, vol. 15, American Chemical Society.

Roman Jr. et al, Organometallics, 1997, p. 1484-1490, vol. 16, American Chemical Society.

Tugcu et al, Industrial and Engineering Chemical Research, 2002, p. 6482-6492, vol. 41, American Chemical Society.

Wyatt et al, European Journal of Organic Chemistry, 2003, p. 4216-4226, Wiley-VCH.

Yamamoto et al, Chemistry Letters, 1984, p. 1603-1606, vol. 7.

Yamamoto et al, Chemistry Letters, 1989, p. 349-352, vol. 1.

PCT/US09/030553 International Search Report, Jun. 15, 2009.

PCT/US09/030553 Written Opinion of the International Search Authority, Jun. 15, 2009.

PCT/US09/030553 International Preliminary Report on Patentability, Jul. 20, 2010.

* cited by examiner

Synthetic Sequence for Ligand A
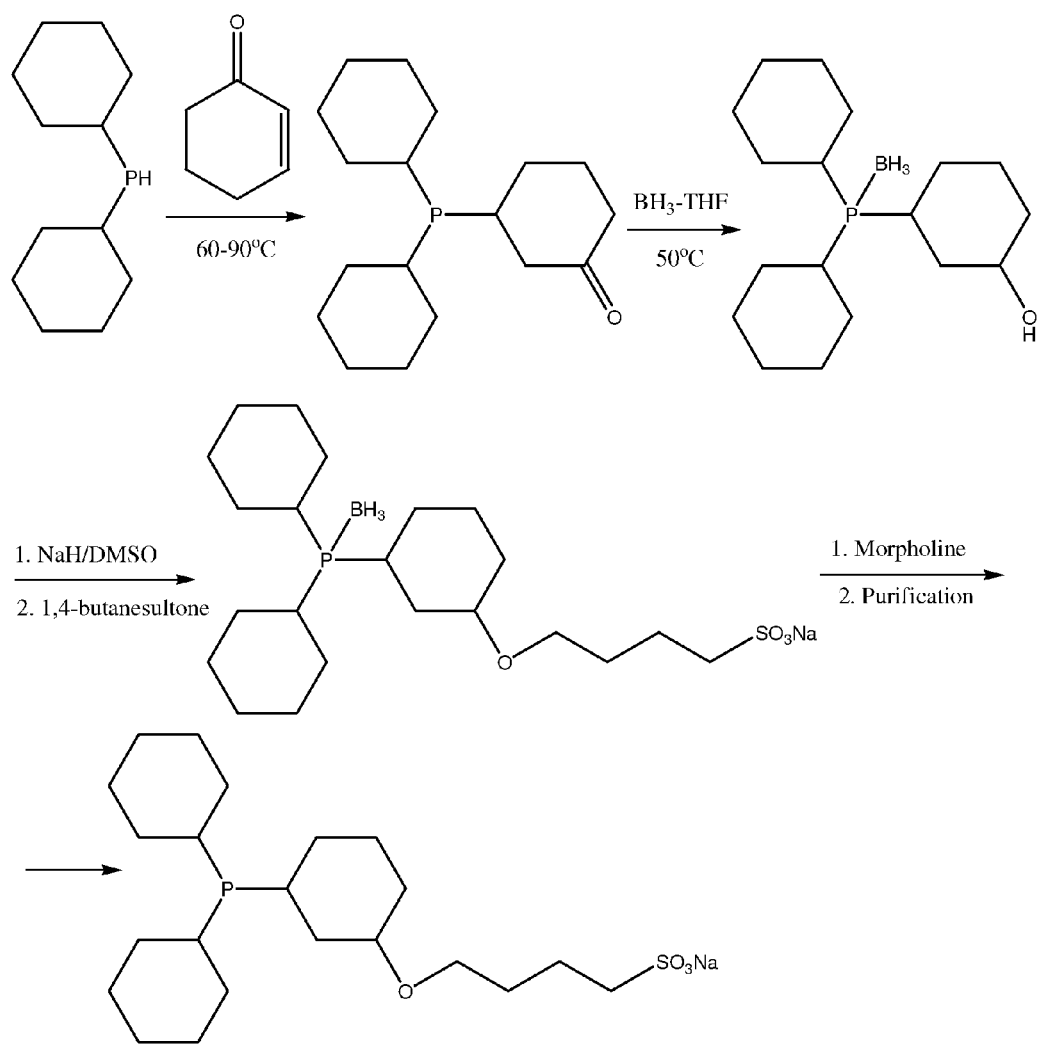

SULFONATED ORGANOPHOSPHINE COMPOUNDS AND USE THEREOF IN HYDROFORMYLATION PROCESSES

CROSS-REFERENCE TO RELATED APPLICATION

This application claims the benefit of U.S. Provisional Application Ser. No. 61/021,068, filed Jan. 15, 2008.

BACKGROUND OF THE INVENTION

This invention pertains to a novel class of sulfonated organophosphine compounds and their use as ligands in metal-ligand complex catalysts that are capable of catalyzing hydroformylation processes.

Hydroformylation processes are well known in the art, for example, as described in "Applied Homogeneous Catalysis with Organometallic Compounds," edited by B. Cornils and W. A. Herrmann, VCH, New York, 1996, vol. 1, pp. 29-104. Hydroformylation involves conversion of an olefinically-unsaturated reactant with carbon monoxide and hydrogen (syngas) to produce one or more corresponding formyl-substituted products (aldehydes). Hydroformylation processes are known to be catalyzed by metal-ligand complex catalysts, preferably, a transition metal-organophosphorus ligand complex catalyst. Representative art disclosing hydroformylation catalysts comprising a variety of triorganophosphine, triorganophosphite, diorganophosphite, and bisphosphite ligands is found in the following reference "Rhodium Catalyzed Hydroformylation," edited by P. W. N. M. van Leeuwen and C. Clayer, Kluwer Academic Publisher, USA Edition, 2002. If desired, the formyl-substituted products can be subjected to downstream functionalization processes, for example, reduction of the aldehyde to form an alcohol; or reductive amination of the aldehyde to from an amine; or oxidation of the aldehyde to form a carboxylic acid; or aldolization of the aldehyde followed by oxidation to form an hydroxyacid. Alcohols, amines, carboxylic acids, and hydroxyacids obtained via hydroformylation of an olefinically-unsaturated reactant find utility as solvents, surfactants, and monomers for the preparation of polymers, and as intermediates in the synthesis of pharmaceuticals and other industrially-useful chemicals. Preferably, mono-, di-, and tri-alcohols and corresponding amines obtained directly from hydroformylation can be converted via transesterification into polyester polyols and polyester polyamines, respectively, which are especially useful in the manufacture of polyurethane polymers.

The hydroformylation of long-chain olefinically-unsaturated reactants having from 6 to about 60 carbon atoms is of present day interest. In particular, one class of long-chain olefinically-unsaturated reactants comprises a mixture of mono-, di-, and tri-unsaturated fatty acids or fatty acid esters having from about 10 to about 50 carbon atoms, preferably, the olefinically-unsaturated fatty acid esters of lower alkanols, preferably, $C_{1-8}$ alkanols (mono-alkanols), for example, methanol. Olefinically-unsaturated fatty acid esters of the lower alkanols are themselves derived by transesterifying a seed oil, for example, a soy, castor, or canola vegetable oil, with the $C_{1-8}$ alkanol. Thus, seed oils can provide a renewable alternative feedstock of olefinically-unsaturated fatty acids or fatty esters, which is capable, in part, of replacing petroleum in the manufacture of industrially-useful chemicals.

More specifically, the present day hydroformylation of olefinically-unsaturated fatty acids or fatty esters and other long chain olefinically-unsaturated compounds is conducted in a rhodium-catalyzed one-phase process containing a water-soluble ionic ligand, preferably, an alkali metal salt of a dihydrocarbylarylphosphine monosulfonate compound wherein the hydrocarbyl comprises an alkyl or aryl group, and further containing a solubilizing solvent, such as N-methyl-2-pyrrolidinone (NMP), as disclosed for example in WO 2004/096744. Separation of the resulting aldehyde-containing reaction product fluid is advantageously effected by addition of water, as disclosed for example in U.S. Pat. No. 5,180,854, under conditions sufficient to obtain a non-polar phase containing one or more aldehyde products and any non-polar solvent(s) as may be present and a polar phase containing the rhodium-ligand catalyst, optional free ionically-charged ligand, water, and solubilizing solvent. Disadvantageously, ligands containing an aryl-phosphorus bond tend to undergo alkyl-aryl exchange during the course of hydroformylation by way of reaction of the phosphine ligand with the olefinically-unsaturated compound, as disclosed in U.S. Pat. No. 4,283,304 and by A. G. Abatjoglou, et al., in *Organometallics*, 1984, 3, 923-926.

Ligand alkyl-aryl exchange generates three undesirable results. First, alkyl-aryl exchange consumes the particular species of ligand active in the hydroformylation process, which then needs to be replaced. Second, alkyl-aryl exchange produces non-ionic or neutral ligands, which are insoluble in water and which can remain along with coordinated rhodium complexes in the non-polar phase containing the aldehyde product(s) rather than being extracted into the polar phase. Third, alkyl-aryl exchange produces sodium benzenesulfonate, which accumulates in the polar phase and can eventually precipitate onto the walls of the reactor equipment and foul the same. Sodium benzenesulfonate may also induce undesirable separation of the water/NMP polar phase.

In view of the above, a search continues to discover novel compounds that can be utilized as ligands in transition metal-ligand complex catalysts for the hydroformylation of olefinically-unsaturated compounds, particularly, unsaturated fatty acids and fatty esters and other long-chain olefinically unsaturated compounds. It would be desirable for such novel compounds to provide for comparable or better olefin conversion and product selectivity, as compared with prior art organophosphorus ligands. Moreover, it would be desirable for such novel compounds to provide for improved ligand stability with reduction of alkyl-aryl exchange, as compared with prior art ligands.

U.S. Pat. No. 5,773,666 discloses a hydroformylation process using $P(X_1)(X_2)(X_3—SO_3M)$ as a ligand, wherein $X_1$ and $X_2$ are monovalent hydrocarbon groups with 1-15 carbon atoms, $X_3$ is a divalent hydrocarbon group with 1-15 carbon atoms, and M is an alkali metal. In the description and working examples of U.S. Pat. No. 5,773,666, $X_3$ is disclosed to be specifically 1,3-phenylene or a tri- or tetra-methylene, such that the phenylene or the tri- or tetra-methylene is substituted with a sulfonate group.

U.S. Pat. No. 5,180,854 discloses sulfonated organophosphine ligands of the following generic formula:

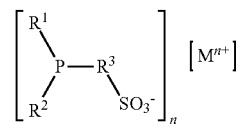

wherein $R^3$ represents a divalent alkylene radical having from 2 to 12 carbon atoms or a divalent 1,3-phenylene radical.

Preferably, when R³ is a divalent alkylene radical, R³ has from 2 to 5 carbon atoms; more preferably, R³ is, 1,3-propylene or 1,4-butylene.

T. Barak, et al. discloses in *Organometallics,* 12 (1993), 164-170, water-soluble phosphines prepared by sulfonating one or more phenyl groups on a tri(aralkyl)phosphine of the formula $P[(CH_2)_x(C_6H_5)]_3$, wherein x is 1, 2, 3, or 6.

U.S. Pat. No. 4,625,068 and U.S. Pat. No. 4,642,388 disclose the use of non-ionic tricycloalkylphosphines, such as tricyclohexylphosphine, in hydroformylation of internal olefins or hindered terminal vinylidenes, respectively.

SUMMARY OF THE INVENTION

In one aspect, this invention provides for a novel class of sulfonated triorganophosphine compounds represented by Formula I:

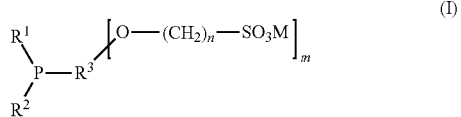

(I)

wherein R¹ and R² each individually represents a monovalent hydrocarbyl or substituted hydrocarbyl radical selected from alkyl, aralkyl, and alicyclic radicals; wherein R³ represents a divalent or polyvalent alkylene or alicyclic radical (hereinafter, "alkylene radical"), which is bonded to the phosphorus atom and to one or more sulfonate substituents via an alkylether link, and further wherein R³ does not contain any aryl moieties; n is an integer reflecting a number of methylene groups in the alkylether link, advantageously from 1 to about 5; M represents a monovalent cation; and m is an integer representing a total number of sulfonated alkylether substituents bonded to R³, advantageously, from 1 to about 3. As a further requirement, each of R¹, R², and R³ are "bulky" groups, which means that in each of R¹, R², and R³ the carbon atom attached to the phosphorus atom or a carbon atom directly bonded to the carbon atom attached to the phosphorus atom is additionally bonded to at least 2 other carbon atoms. The aforementioned requirement ensures that R¹, R², and R³ have branching carbon chains that provide for steric bulk.

In a second aspect, this invention provides for a novel complex catalyst or complex catalyst precursor composition comprising a Group 8-10 (formerly Group VIII) transition metal bonded to at least one molecule of ligand comprising Formula I hereinabove, the transition metal optionally being further bonded to carbon monoxide, hydrogen, or both carbon monoxide and hydrogen.

In a third aspect, this invention provides for a novel complex catalyst solution or complex catalyst precursor solution comprising a solvent, a complex catalyst or catalyst precursor composition comprising a Group 8-10 transition metal bonded to at least one molecule of ligand, and optionally further comprising free ligand, wherein the bonded and free ligands are represented by Formula I hereinabove; and wherein optionally the Group 8-10 transition metal can be further bonded to carbon monoxide, hydrogen, or both carbon monoxide and hydrogen.

The following advantages of the invention are mentioned; but should not in any manner place limits on the invention. At the start, the ionically-charged class of compounds claimed herein possesses sufficient water solubility or solubility in appropriate mixtures of water and non-aqueous polar solvents, such that said ionically-charged compound(s) can be easily separated from one or more non-polar reaction products. The separation involves addition of water to the product fluid with subsequent formation of two immiscible liquid phases, one of which is the product phase and the other of which is the catalyst-containing phase. This advantage renders the claimed class of compounds useful for certain hydroformylation processes detailed hereinafter. Accordingly, the novel catalyst composition and novel solution claimed herein comprising the ionically-charged ligand composition of this invention find utility, particularly, in the hydroformylation of long-chain olefinically-unsaturated compounds having from 6 to about 60 carbon atoms, preferably, from about 10 to about 50 carbon atoms, such as, olefinically-unsaturated fatty acids or fatty esters derived from seed oils. Beneficially, the novel hydroformylation catalyst of this invention provides for comparable olefin conversion and product selectivity as compared with prior art catalysts containing ionically-charged ligands. Moreover, the novel composition provides for improved ligand stability and improved ligand and rhodium recovery and recycling, as compared with prior art ligands containing one or more aryl-phosphorus bonds. Indeed, one of the essential decomposition mechanisms of the prior art ligands involves alkyl-aryl exchange by reaction of an olefin with the aryl radical directly attached to the phosphorus atom. The class of compounds claimed in this invention does not comprise an aryl-phosphorus bond, but rather contains phosphorus bonded only to bulky alkyl groups, thereby essentially eliminating the possibility of alkyl-aryl exchange. Additionally, the bulky alkyl groups R¹, R², and R³ provide for acceptable ligand concentration effect on process reaction rate, which means that a change in ligand concentration does not unacceptably alter the reaction rate.

In a fourth aspect, this invention provides for a novel hydroformylation process comprising contacting one or more olefinically-unsaturated compounds with carbon monoxide and hydrogen in the presence of a Group 8-10 transition metal-ligand complex catalyst, wherein the ligand is represented by the composition of Formula I hereinabove, the contacting being conducted under process conditions sufficient to prepare one or more corresponding aldehyde products. The novel hydroformylation process of this invention finds utility in the production of useful organic intermediates, solvents, and monomers, particularly, mono-, di-, and tri-alcohols and amines. These monomers can be converted via transesterification into polyester polyols and polyester polyamines that find utility in the manufacture of polyurethane polymers.

BRIEF DESCRIPTION OF THE DRAWING

FIG. 1 illustrates a synthetic scheme for preparing sodium 4-[3-(dicyclohexylphosphino)cyclohexyloxy]butane-1-sulfonate.

DETAILED DESCRIPTION OF THE INVENTION

Certain phrases, terms, and words used in this application are defined hereinafter. When interpreting a meaning of a phrase, term, or word, its definition here governs, unless for a particular use, a different meaning is stated elsewhere in this specification or unless a context of the use of the phrase, term, or word clearly indicates a different meaning is intended from the definitions provided herein.

The articles "a" and "the" refer to singular and plural forms of what is being modified by the articles. When used in front of a first member of a list of two or more members, the words "a" and "the" independently refer to each member in the list. As used herein, "a," "an," "the," "at least one," and "one or more" are used interchangeably. The term "comprises" and variations thereof do not have a limiting meaning where these terms appear in the description and claims. Thus, for example, a reactant mixture that comprises an olefin can be interpreted to mean that the olefin includes one or more olefins.

All percentages, preferred amounts or measurements, ranges and endpoints thereof are inclusive, that is, "a range from 5 to 10" includes 5 and 10. "At least" is equivalent to "greater than or equal to," and "at most" is, thus, equivalent to "less than or equal to." Numbers herein have no more precision than stated. Thus, "115" includes at least from 114.6 to 115.4. All ranges from a parameter described as "at least," "greater than," "greater than or equal to" or similarly, to a parameter described as "at most," "up to," "less than," "less than or equal to" or similarly are preferred ranges regardless of the relative degree of preference indicated for each parameter. Thus, a range that has an advantageous lower limit combined with a most preferred upper limit is preferred for the practice of this invention. The term "advantageously" is used to denote a degree of preference more than required, but less than is denoted by the term "preferably."

Unless stated otherwise, when an element, material, or step capable of causing undesirable effects is present in amounts or in a form such that it does not cause the effect to an unacceptable degree, that element, material, or step is considered substantially absent for the practice of this invention. Those skilled in the art recognize that acceptable limits vary with equipment, conditions, applications, and other variables, but are determinable without undue experimentation in each situation where they are applicable. In some instances, variation or deviation in one parameter is acceptable to achieve another desirable end.

As used herein, the phrase "having the formula" or "represented by the formula" is not intended to be limiting and is used in the same manner as the term "comprising" is commonly used.

The term "comprising," is synonymous with "including," "containing," or "characterized by," is inclusive or open-ended and does not exclude additional, unrecited elements, material, or steps. The term "consisting essentially of" indicates that in addition to specified elements, materials, or steps, unrecited elements, materials or steps are optionally present in amounts that do not unacceptably materially affect at least one basic and novel characteristic of the subject matter. The term "consisting of" indicates that only stated elements, materials or steps are present except that unrecited elements, materials or steps are optionally present to an extent that has no appreciable effect, or are substantially absent.

The word "optionally" means "with or without," that is, not mandatory and left to one's choice. As an example, to say "optionally, a non-polar solvent" means with or without a non-polar solvent.

The number of carbon atoms or a range thereof forming a moiety or compound is defined by prefixing the moiety or compound with a formula "$C_m$" or "$C_m$-$C_n$," respectively, wherein m and n are integers. For example, a $C_1$-$C_{10}$ hydrocarbyl means the hydrocarbyl has a number of carbon atoms in a range from one (1) to ten (10) carbon atoms.

Abbreviations and symbols "g," "h," "L," "ml," "mol," "mmol," "NMR," "° C.," "psia (kPa)," and "%" are used, respectively, for "gram," "hour" "liter," "milliliter," "mole," "millimole," "nuclear magnetic resonance," "degree Celsius," "pounds per square inch absolute (kilopascals), and "percent," respectively, and plural forms thereof.

For the purposes of this invention, all citations herein to chemical Group(s) and elements are referenced with respect to *IUPAC Nomenclature of Inorganic Chemistry: IUPAC Recommendations* 2005, Royal Society of Chemistry, 2005, edited by N. G. Connelly and T. Damhus. (For correspondence with former recommendations, see Periodic Table of the Elements, *CRC Handbook of Chemistry and Physics, 75th* ed., CRC Press, 1994.)

The relevant teachings of each reference cited herein are incorporated to the maximum extent allowed by United States law. In the event of a conflict between a portion of an incorporated reference and this application, this application takes precedence.

In the detailed description that follows, several chemical terms are frequently used, which for clarity are defined herein.

The term "hydrocarbyl" refers to univalent organic radicals comprised of carbon and hydrogen atoms and containing from about 1 to about 30 carbon atoms, preferably, from 1 to about 12 carbon atoms, including linear, branched, cyclic, saturated and unsaturated species, such as alkyl, alicyclic, alkenyl, aryl, alkaryl, and aralkyl groups. The term "substituted hydrocarbyl" refers to a hydrocarbyl radical that is substituted with one or more substituents disclosed hereinafter, such that a hydrogen atom attached to a carbon atom is replaced by a non-hydrogen atom or a non-hydrogen-containing substituent, for example, a halogen (e.g., F, Cl, Br), nitrogen, oxygen, or phosphorus.

The term "hydrocarbylene" refers to a divalent hydrocarbyl radical.

The term "alkyl" refers to a saturated monovalent hydrocarbyl radical, which can be linear, branched, or cyclic (alicyclic). If linear or branched, the radical advantageously contains from 1 to about 30 carbon atoms, for example, methyl, ethyl, propyl, isopropyl, n-butyl, iso-butyl, tert-butyl, and the like. If cyclic (alicyclic), the radical advantageously contains from 4 to about 8 carbon atoms, such as cyclobutyl, cyclopentyl, cyclohexyl, cycloheptyl, and cyclooctyl. Preferably, the linear or branched alkyl radical contains from about 1 to about 12 carbon atoms; and the alicyclic radical contains from about 5 to about 7 carbon atoms, exclusive of carbon-containing substituents.

The term "alkylene" as used herein refers to a linear, branched, or cyclic divalent alkyl radical.

As used herein the term "aromatic" refers to a polyatomic, cyclic, conjugated ring system containing (4δ+2) π-electrons, wherein δ is an integer greater than or equal to 1. The term "fused" as used herein with respect to a ring system containing two or more polyatomic, cyclic rings means that with respect to at least two rings thereof, at least one pair of adjacent atoms is included in both rings. The term "aryl" refers to a monovalent aromatic substituent which may be a single aromatic ring or multiple aromatic rings that are fused together, linked covalently, or linked to a common group such as a methylene or ethylene moiety. Examples of aromatic ring(s) include phenyl, naphthyl, anthracenyl, and biphenyl, among others. Preferred aryl radicals contain one aromatic ring.

The term "arylene" refers to a divalent aryl radical.

The term "aralkyl" or "arylalkyl" refers to a monovalent alkyl radical substituted with at least one aryl radical. The term "aralkylene" refers to a divalent alkylene radical substituted with at least one aryl radical.

The term "arylalicyclic" refers to an alicyclic radical substituted with at least one aryl group. An example of an arylalicyclic radical is "phenylcyclohexyl" or "phenylcyclopentyl." Advantageously, the arylalicyclic radical contains greater than about 10 carbon atoms and less than about 20 carbon atoms.

The term "alkaryl" refers to a monovalent aryl radical with one or more alkyl substituents. The term "alkarylene" refers to a divalent aryl radical with one or more alkyl substituents.

The term "alkoxy" refers to an alkyl radical bonded at one end to an oxygen atom. When the oxygen atom is further bonded to a second alkyl or cycloaliphatic radical, then the group is referred to as an "alkylether linkage."

As used herein, any and all of the terms "hydrocarbyl," "hydrocarbylene," "alkyl," "alkylene," "aromatic," "aryl," "arylene," "alkaryl," "alkarylene," "aralkyl," "aralkylene," "alicyclic," "arylalicyclic," and "alkoxy" are intended to include substituted variants thereof. The term "substituted" or the words "substituted variants thereof" refer to the replacement of at least one hydrogen atom that is bonded to a carbon atom, for example, an alkyl or aryl carbon atom, with a non-hydrogen moiety, for example, a heteroatom or heteroatom-containing substituent, for example, a halogen (preferably, F), nitrogen, oxygen, or phosphorus.

In the detailed description herein, it is frequently noted that "alkoxy" radical is substituted with one or more sulfonate ions. The presence of one or more substituents on any particular radical will increase the valency of that radical by one or more. For example, if a divalent alkylene radical, e.g., $R^3$, is substituted with one or more substituents, the valency of the alkylene radical will increase to trivalent or polyvalent, respectively. Other substituents that may be present on any of the radicals include, without limitation, functional groups such as halogen, phosphonyl, $C_{1-20}$ alkylamido, imino, hydroxyl, $C_{1-20}$ alkoxy, $C_{5-20}$ aryloxy, $C_{2-20}$ alkoxycarbonyl, $C_{5-20}$ aryloxycarbonyl, formyl, acyl, cyano, cyanato, carbamoyl, epoxy, silyl, silyloxy, silanyl, siloxazanyl, and the hydrocarbyl moieties $C_{1-20}$ alkyl, $C_{2-20}$ alkenyl, $C_{2-20}$ alkynyl, $C_{5-20}$ aryl, $C_{5-30}$ aralkyl, and $C_{5-30}$ alkaryl; preferably, cyano, fluoro, trifluoromethyl, trialkylsilyl, alkoxy, carboalkoxy (ester), dialkyl amino, dialkylamido, more preferably, where appropriate in the aforementioned preferred list having $C_{1-15}$ carbon atoms. In addition, the aforementioned functional groups can, if a particular group permits, be further substituted with one or more additional functional groups or with one or more hydrocarbyl moieties, such as those specifically enumerated above.

In one aspect, this invention provides for a novel class of sulfonated triorganophosphine compounds represented by Formula I:

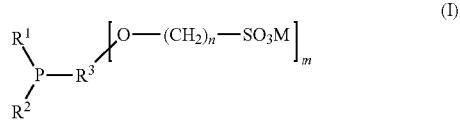

wherein $R^1$ and $R^2$ each individually represent a monovalent hydrocarbyl or substituted hydrocarbyl radical selected from alkyl, aralkyl, and alicyclic radicals; wherein $R^3$ represents a divalent or polyvalent alkylene or alicyclic radical (alternatively, "alkylene radical"), which is bonded to the phosphorus atom and to one or more sulfonate substituents via an alkoxy link, and further wherein $R^3$ does not contain any aryl moieties; n is an integer representing a number of methylene groups in the alkoxy link, advantageously from 1 to about 5; M represents a monovalent cation; and m is an integer representing a total number of sulfonated alkoxy substituents bonded to $R^3$, advantageously, from 1 to about 3. As a further requirement, each of $R^1$, $R^2$, and $R^3$ are "bulky" groups, which means that in each of $R^1$, $R^2$, and $R^3$ the carbon atom attached to the phosphorus atom or a carbon atom directly bonded to the carbon atom attached to the phosphorus atom is additionally bonded to at least 2 other carbon atoms. The aforementioned requirement ensures that $R^1$, $R^2$, and $R^3$ have branching carbon chains that provide for steric bulk. While not intending to bind the invention to any theory, it is believed that the bulky radicals may provide for hydroformylation catalysts comprising only one organophosphine ligand per transition metal atom (as opposed to a plurality of ligands per transition metal atom), which in turn may lead to improved catalyst activity.

In a preferred embodiment, $R^1$ and $R^2$ each individually represent a monovalent hydrocarbyl or substituted hydrocarbyl radical containing from 3 to about 30 carbon atoms selected from alkyl, aralkyl, and alicyclic monovalent radicals, with branching at the carbon attached to the phosphorus atom or branching at the carbon adjacent to the carbon attached to the phosphorus atom so as to provide for steric bulk. More preferably, the alkyl radicals contain from 3 to about 12 carbon atoms, while the aralkyl radicals contain from about 6 to about 12 carbon atoms. The alicyclic radicals can be mono-cyclic, bi-cyclic, or poly-cyclic and preferably, contain from about 3 to about 10 carbon atoms, exclusive of carbon-containing substituents on the ring(s). An illustrative, but non-limiting, list of alkyl radicals represented by the $R^1$ and $R^2$ includes iso-propyl, iso-butyl, sec-butyl, tert-butyl, 2,2-dimethylpropyl, 2-methylbutyl, 1,1-dimethylpropyl, 2-ethylhexyl. Aralkyl radicals include, without limitation, benzyl, 1-phenylethyl, phenylcyclohexyl, 1,2,3,4-tetrahydronaphthyl, phenylcyclopentyl; alicyclic radicals include, without limitation, cyclopentyl, cyclohexyl, cycloheptyl, cyclooctyl, ethylcyclohexyl, norbornyl, adamantyl, and dicyclopentyl. Moreover, such monovalent hydrocarbon radicals can be substituted with any substituent that does not adversely change the desired result(s) of this invention. Illustrative substituents that can be bound to the monovalent hydrocarbyl radical include those substituents mentioned hereinabove, preferably, cyano, fluoro, trifluoromethyl, trialkylsilyl, alkoxy, carboalkoxy (ester), dialkyl amino, and dialkylamido, preferably, having 1 to 12 carbon atoms where appropriate. Even more preferably, $R^1$ and $R^2$ are each individually selected from branched chain alkyl radicals having from 3 to 10 carbon atoms (such as iso-propyl, iso-butyl, neo-pentyl, etc.), cyclohexyl, norbornyl, and adamantyl. Most preferably, $R^1$ and $R^2$ each individually represents a cyclohexyl or iso-propyl radical, especially, cyclohexyl.

Preferably, $R^3$ in Formula I is selected from divalent and polyvalent alicyclic and alkylene radicals having greater than 3 carbon atoms and advantageously less than 10 carbon atoms, which optionally can be substituted with substituents such as those mentioned above, preferably, halide, alkoxy, cyano, and/or alkyl groups. $R^3$ is further required to be connected to at least one sulfonate ($—SO_3^-$) ion via an alkoxy link to the $R^3$ group. A non-limiting list of $—OR^3$ diradicals (polyradicals) suitable for this invention is set forth hereinafter.

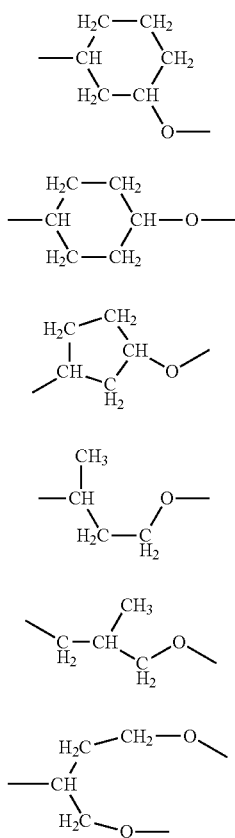

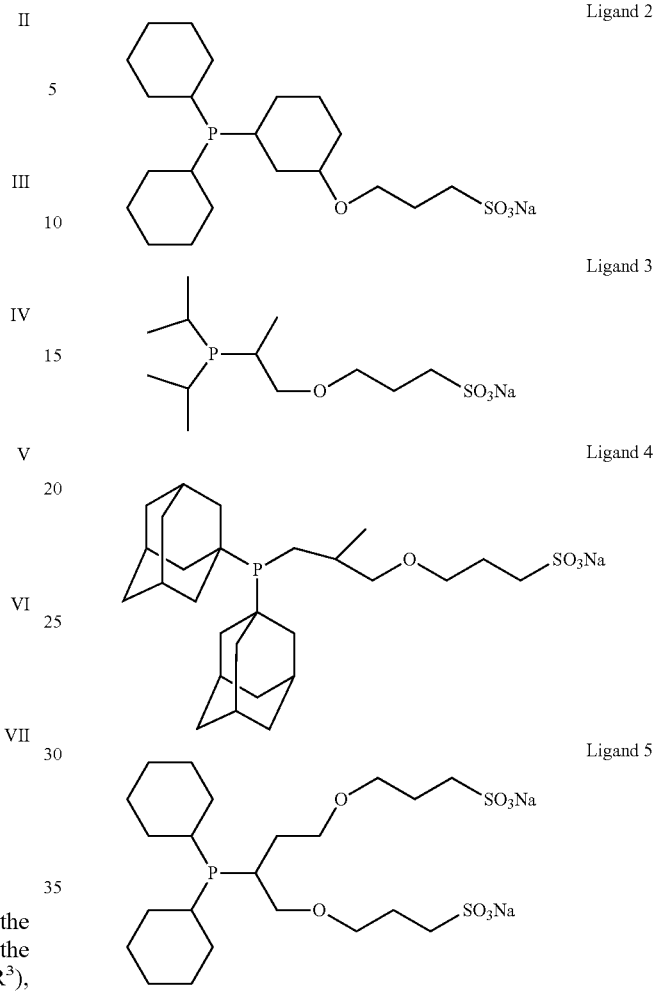

For sake of clarity, it should be mentioned that in the radicals R³ illustrated hereinabove, the oxygen atom of the alkoxy group is shown, that is, added to the formula (—OR³), to clarify the orientation of the radical in the claimed composition. Moreover, it should be understood that the terminal bond pendent from the carbon atom in the illustrated species is connected to the phosphorus atom.

Preferably, n in Formula I is 3 or 4. Preferably, M in Formula I represents a monovalent metal cation selected from the group consisting of alkali metal ions. Illustrative alkali metal ions include lithium (Li⁺), sodium (Na⁺), potassium (K⁺), rubidium (Rb⁺), and cesium (Cs⁺). Preferably, M is sodium or potassium ion. Moreover as noted above, m is preferably 1 or 2.

Preferred sulfonated tertiary organophosphine metal salt compounds of Formula I include the following:

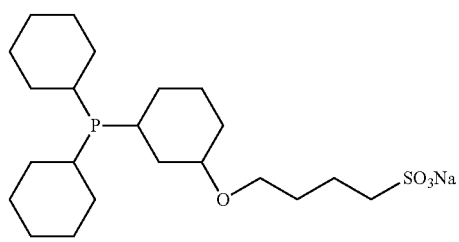

The ionically-charged triorganophosphine compound (I) of this invention can be synthesized in a four-step process. The first step comprises addition of dihydrocarbylphosphine across the double bond of an unsaturated ketone (enone), for example, 2-cyclohexene-1-one, to form a (dihydrocarbylphosphino)alkylketone. A general procedure is described in International Patent Application Publication 2004/094440, incorporated herein by reference. The second step is a simultaneous reduction of the keto group and protection of the phosphino group with borane, so as to form a (dihydrocarbylphosphino)alkanol-borane. A general procedure for the second step is presented by J. McNulty and Y. Zhou, *Tetrahedron Letters*, 2004, 45, 407-409, incorporated herein by reference. In contrast to unprotected phosphines, phosphine-boranes are effectively resistant to oxidation. The third step involves metalation of the phosphine-borane with sodium hydride followed by reaction with an alkane sultone, which results in opening of the sultone cycle and formation of a borane-protected (dihydrocarbylphosphino)hydrocarbyloxy alkane sulfonate. The general procedure for the reaction of alcohols with sultones has been reported previously in *Industrial Engineering & Chemical Research*, 2002, 41, 6482-6492, incorporated herein by reference. In the fourth step, the borane group is cleaved, preferably by morpholine at about 110° C.±5° C., and the resulting (dihydrocarbylphosphino)hydrocarbyloxy alkane sulfonate is purified. Purification involves (a) conversion of the material to its acidic form (zwitterion)

with acid, such as sulfuric acid; (b) extraction of the zwitterion with a chlorinated hydrocarbon, such as methylene chloride; and (c) neutralization of the extracted zwitterion with a stoichiometric amount of base, preferably, sodium hydroxide. (The term "zwitterion" (from the German "Zwitter"—"hybrid," "hermaphrodite") is a chemical compound that is electrically neutral but carries formal positive and negative charges on different atoms. In this instance, the phosphorus atom is protonated and carries a +1 charge, while a sulfonate ion is deprotonated and carries a −1 charge.) The overall synthetic scheme is illustrated in FIG. 1 for a representative compound, namely, sodium 4-[3-(dicyclohexylphosphino)cyclohexyloxy]butane-1-sulfonate.

The isolated compounds of this invention can be identified by standard analytical techniques known to the skilled person, for example, $^{31}P$ and/or $^{1}H$ and/or $^{13}C$ nuclear magnetic resonance spectroscopy (NMR), mass spectrometry (MS), and/or infrared spectroscopy. The purity of the compounds and any intermediates of the synthesis can be verified by gas chromatography (GC), thin layer chromatography (TLC), high performance liquid chromatography (HPLC), any suitable NMR spectroscopy, including $^{1}H$, $^{13}C$, and $^{31}P$ NMR, and ionic chromatography (IC).

Referring again to FIG. 1, the synthetic scheme is described in greater detail. In the first step, a secondary dihydrocarbylphosphine is added across the double bond of an unsaturated ketone (enone), as disclosed in International Patent Application Publication 2004/094440. A suitable list of secondary dihydrocarbylphosphines include, without limitation, any of those corresponding to the generic formula $R^1R^2PH$, wherein $R^1$ and $R^2$ have the definitions noted hereinbefore. Preferably, the dihydrocarbylphosphine is selected from dicyclohexylphosphine, diisopropylphosphine, diisobutylphosphine, dicycloheptylphosphine, dicyclopentylphosphine, dinorbornylphosphine, and diadamantylphopsphine. The unsaturated ketone (enone) can be any such compound that provides for a precursor to the desired $R^3$ radical attached to an oxygen atom of the ether linkage. For example, if the desired $R^3$ radical is cyclohexylene, then the enone to be reacted with the secondary phosphine is 2-cyclohexenone. Other enones that can be suitably employed include, without limitation, 2-cyclopentenone, 3-penten-2-one, 4-hexen-3-one, 3-hexen-2-one, 5-methyl-3-hexen-2-one and crotonaldehyde. The enone is added stoichiometrically or in a small excess relative to the secondary phosphine. A 10-20 percent excess is more than sufficient. The reaction is advantageously conducted in a liquid phase, with or without a solvent as desired, at a temperature advantageously between about 40° C. and about 180° C., preferably, between about 50° C. up to about 100° C., more preferably, between about 60° C. and 90° C. The reaction is advantageously complete within about 8 hours or less, but at least about 30 minutes. The solvent, if used, can comprise any solvent that does not interfere with the reaction, suitable solvents being, for example, toluene, ethanol, isopropanol, butanol, dimethylformamide, tributylphosphate, and tributylphosphine oxide, preferably, dimethylformamide. The reaction product comprises a (dihydrocarbylphosphino)alkylketone, which can be separated from the reaction medium via any conventional method, such as distillation, preferably, under reduced pressure. The reaction is preferably conducted under an inert atmosphere of nitrogen or helium or argon gas; and any solvent employed is degassed of oxygen.

The second step comprises a simultaneous reduction of the keto group and protection of the phosphino group with borane, so as to form a (dihydrocarbylphosphino)-alkanol-borane, as described by J. McNulty and Y. Zhou, *Tetrahedron Letters,* 2004, 45, 407-409. Advantageously, the (dihydrocarbylphosphino)alkylketone is dissolved in a suitable solvent as noted hereinbefore for the first step, and then contacted with borane ($BH_3$), provided in solution of solvent, advantageously, the same solvent as used in the first step. Tetrahydrofuran is a preferred solvent. The quantity of borane used is advantageously in stoichiometric excess over the phosphine because borane is used for both phosphine protection and ketone reduction; advantageously a molar ratio of borane to phosphine ranging from about 2/1 to about 3/1 is employed. The borane is added slowly in aliquots while cooling the solution containing the phosphine by any conventional cooling method, such as, submersion in a sodium chloride ice-bath. The reaction solution is then stirred for a time from about 8 to about 20 hours, then heated at a temperature from about 40° C. to 70° C. for a period from about 8 to about 30 hours. The reaction with borane is conducted under an inert gas atmosphere, such as nitrogen, helium, or argon; all reagents being degassed prior to use. Afterwards, water is added to the reaction mixture and the reaction medium is extracted with a water-immiscible solvent, such as diethyl ether. The water-immiscible layer is extracted and washed with water several times to ensure removal of all water-soluble species. The resulting organic phase is dried over a suitable drying agent, such as magnesium sulfate, and the water-immiscible solvent is removed via distillation. The resulting solid product comprises the (dihydrocarbylphosphino)alkanol-borane of generic formula $R^1R^2P(BH_3)R^3OH$, wherein $R^1$, $R^2$, and $R^3$ have the definitions noted hereinbefore.

The third step involves metalation of the phosphine-borane, preferably, with sodium hydride, followed by reaction with an alkane sultone, which results in opening of the sultone cycle and formation of a (dihydrocarbylphosphino)hydrocarbyloxy alkane sulfonate. All operations are conducted under an inert atmosphere, for example, nitrogen, argon, or helium; and all reagents are degassed. Advantageously, the phosphine-borane is dissolved in a suitable deoxygenated, non-aqueous polar solvent, such as dimethylsulfoxide. The solution is then added slowly to a slurry of metalating agent, preferably sodium hydride, in a suitable deoxygenated, non-aqueous polar solvent, preferably, the same solvent as used for the phosphine-borane, and more preferably, dimethyl sulfoxide. The metalating agent, or sodium hydride, is employed in a stoichiometric excess relative to phosphine-borane. Advantageously, a molar ratio of metalating agent to phosphine-borane ranging from about 1.10/1 to about 3/1 is preferred. The reaction medium is stirred for a time from about 8 to about 24 hours at a temperature ranging from about room temperature (taken as 21° C.) to about 40° C. The resulting (dihydrocarbylphosphino)alcoholate-borane is sulfonated by reaction with an alkane sultone, so as to form a sulfonated product with an alkyl ether linkage. The procedure for the reaction of alcohols with sultones is described in *Industrial Engineering & Chemical Research,* 2002, 41, 6482-6492. Thus, at the end of the metalation reaction to form the (dihydrocarbylphosphino)alcoholate-borane, an alkane sultone is added to the reaction medium. The alkane sultone has the general formula shown below, where p=3, 4, or 5.

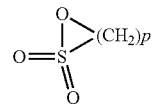

Suitable alkane sultones include, without limitation, 1,3-propanesultone, 1,4-butanesultone, 1,5-pentanesultone and the like. The quantity of alkylene sultone is employed in a slight stoichiometric excess ranging from about 1.1 moles to about 1.5 moles per mole of phosphine-borane. An exotherm is usually observed on addition of the sultone, after which the reaction mixture is heated at a temperature ranging from about 40° C. to about 100° C., preferably, from about 60° C. to about 90° C., for a time ranging from about 3 hours to about 10 hours. At the end of the reaction period, reaction medium is worked-up conventionally by distilling off volatile materials and concentrating the product under vacuum distillation, so as to yield a borane-protected (dihydrocarbylphosphino) hydrocarbyloxy alkane sulfonate having the generic formula $R^1R^2P(BH_3)R^3[O—(CH_2)_mSO_3M]_n$, wherein $R^1$, $R^2$, $R^3$, M, m, and n have the definitions given previously.

In the fourth step, the borane group is cleaved, preferably by morpholine, yielding the desired ionically-charged triorganophosphine ligand. The cleavage of the borane is advantageously effected by heating the borane-protected (dihydrocarbylphosphino)-hydrocarbyloxy alkane sulfonate in morpholine at a temperature ranging from about 80° C. to about 140° C., preferably about 110° C.±5° C., for a time ranging from about 1 to about 5 hours. Again, the operation is effected under an inert atmosphere to avoid undue oxidation of the phosphine. The resulting product is advantageously isolated by filtering the reaction medium, then washing the filtered solid with an appropriate organic solvent, such as acetone, and drying in a conventional oven under a flow of inert gas to yield a crude sample of the composition of this invention in acidic form ($M=H^+$). The crude material can be purified by converting the material to its zwitterionic form in dilute aqueous acid, preferably sulfuric acid, advantageously of about 0.01 M to about 0.1 M concentration. The zwitterion is an effectively neutral compound formed from a protonated phosphorus atom and a negatively-charged sulfonate ion. The acidified solution containing the zwitterion is then extracted with a suitable organic solvent, such as a chlorinated hydrocarbon, for example methylene chloride; and from the organic phase the extraction solvent is removed via evaporation, preferably in vacuum, to isolate the zwitterionic form of the compound. As a last step, the zwitterion is re-dissolved in a suitable solvent, advantageously a lower $C_{1-4}$ alkanol, and neutralized with an alcoholic solution of alkali hydroxide, preferably sodium hydroxide in methanol, to convert the zwitterion into the corresponding alkali salt having Formula I. The alkali salt is the catalytically active form of the ligand for carbonylation processes, preferably, hydroformylation.

The composition of this invention of Formula I finds application as a ligand in transition metal complex catalysts and catalyst precursors that are used in carbonylation processes, preferably, hydroformylation processes. Accordingly, in a second aspect this invention provides for an entirely new class of complex catalysts and complex catalyst precursor compositions that comprise a Group 8, 9, or 10 transition metal bonded to at least one ligand represented by Formula I. Optionally, the Group 8-10 transition metal can also be bonded to carbon monoxide, hydrogen, or both carbon monoxide and hydrogen. The Group 8-10 transition metal that makes up the complex catalyst or catalyst precursor composition of this invention includes transition metals selected from the group consisting of rhodium (Rh), cobalt (Co), iridium (Ir), ruthenium (Ru), iron (Fe), nickel (Ni), palladium (Pd), platinum (Pt), and osmium (Os), and mixtures thereof, with the preferred metals being ruthenium, rhodium, cobalt, and iridium, more preferably, rhodium and cobalt, and most preferably, rhodium. The term "complex" as used herein shall be taken to mean a coordination compound formed by the union of one or more ligands, herein one or more ligands of Formula I, with a Group 8-10 metal. Inherently, the ligand(s) is/are electronically rich, since each ligand possesses one phosphorus donor atom having one available or unshared pair of electrons that is capable of forming a coordinate covalent bond independently with the Group 8-10 transition metal. The oxidation state of the Group 8-10 metal can be any available oxidation state, either electronically neutral (zero) or electronically deficient (positive valence) that allows for bonding to the ligand. Moreover, the oxidation state of the Group 8-10 transition metal as well as the overall oxidation state of the coordination complex or complex precursor can vary during use in the hydroformylation process. The number of available coordination sites on the selected Group 8-10 transition metal is well known in the art and can range advantageously from about 4 to about 6. Optionally, the Group 8-10 transition metal can be additionally bonded to carbon monoxide, hydrogen, or both carbon monoxide and hydrogen.

In a third aspect, this invention can be described as a novel transition metal complex catalyst or catalyst precursor solution comprising an organic solvent, a solubilized Group 8-10 transition metal-ligand complex, and optionally, free ligand, wherein the free and bound ligands are represented by Formula I hereinabove. Such novel solutions can be prepared by forming a solution comprising an organic solvent, free ligand, and a Group 8-10 transition metal source material, such as the corresponding transition metal oxide, hydride, carbonyl, salt, or organotransition metal complex described hereinafter; and thereafter subjecting such solution to reaction conditions sufficient to bind at least a portion of the ligand to the Group 8-10 transition metal. Optionally, carbon monoxide and hydrogen can be dissolved in the solution and bonded to the Group 8-10 transition metal.

The Group 8-10 transition metal-ligand complex catalyst of this invention can be synthesized by methods known in the art. For instance, a Group 8-10 transition metal hydrido-carbonyl(ligand) catalyst can be preformed and introduced into the reaction medium of a hydroformylation process. Standard analytical methods can be used to identify the complex catalyst or catalyst precursor composition, including for example, elemental analysis, mass spectroscopy, infrared spectroscopy, and $^1H$, $^{31}P$, and/or $^{13}C$ NMR spectroscopy, and the like.

Preferably, the Group 8-10 transition metal-ligand complex catalyst of this invention is derived from a Group 8-10 transition metal source material that is introduced into the carbonylation reaction medium for in situ formation of the active catalyst. For example, rhodium source materials, such as, rhodium acetylacetonate, rhodium dicarbonyl acetylacetonate, $Rh_2O_3$, $Rh_4(CO)_{12}$, $[RhCl(CO)_2]_2$, $Rh_6(CO)_{16}$, $Rh(NO_3)_3$, and the like can be introduced into the carbonylation reaction medium along with the ligand for the in situ formation of the active catalyst. In a preferred embodiment, rhodium dicarbonyl acetylacetonate is employed as a rhodium source material and reacted with the ligand in the presence of a solvent to form a rhodium-ligand complex catalyst precursor composition, which is introduced into the reactor along with excess free ligand for the in situ formation of the active catalyst. The reaction conditions sufficient for formation of the complex catalyst or catalyst precursor in most cases will be similar to the hydroformylation reaction conditions described hereinbelow.

In a fourth aspect, this invention provides for a carbonylation process, which comprises contacting an organic compound capable of being carbonylated with carbon monoxide under reaction conditions in the presence of the aforementioned Group 8-10 transition metal-ligand complex catalyst wherein the ligand is represented by Formula I. Such processes include the carbonylation of organic compounds, such as olefins, acetylenes, alcohols, and activated chlorides, with carbon monoxide, and optionally, either hydrogen, alcohol, amine, or water, as well as ring closure reactions of functionally unsaturated compounds, for example, unsaturated amides, with carbon monoxide. Exemplary carbonylation processes include, for example, simple carbonylation (insertion of carbonyl in absence of other reactants), hydroformylation, hydroacylation (intermolecular and intramolecular), hydrocyanation, hydroamidation, hydroesterification, and hydrocarboxylation processes. In a preferred embodiment, the carbonylation process also contains free ligand in addition to the ligand bonded to the Group 8-10 transition metal. Preferably, the carbonylation process involves a hydroformylation process, more preferably, the hydroformylation of an olefinically-unsaturated compound with carbon monoxide in the presence of hydrogen and the transition metal-ligand complex catalyst under reaction conditions to prepare one or more corresponding aldehydes (or formyl-substituted product(s)). Hydroformylation is also known under various other names including the "oxo" process, the "oxo" reaction, "oxonation," the "Roelen reaction." The processing techniques employed in the hydroformylation process of this invention correspond to any of the known processing techniques employed in conventional hydroformylation processes, as described hereinafter.

The successful practice of the hydroformylation process of this invention does not depend and is not predicated upon the precise formula of the catalytically active metal complex species, which can be present in a mononuclear, dinuclear, or higher nuclearity form. Indeed, the precise formula of the catalytically active metal ligand complex can be difficult to determine analytically. Although not intended to be bound to any theory or mechanistic discourse, it appears that the active catalytic species in its general form comprises the Group 8-10 transition metal in complex combination with one ligand of Formula I, optionally further in combination with carbon monoxide, since carbon monoxide is also present and capable of complexing to the Group 8-10 transition metal. The ultimate composition of the active complex can also contain one or more additional ligands, such as hydrogen, or an anion satisfying the coordination sites or nuclear charge of the Group 8-10 transition metal obtained advantageously from the starting transition metal material. Illustrative additional ligands include alkyl, aryl, substituted aryl, $CF_3^-$, $C_2F_5^-$, $CN^-$, $R'_2PO^-$, $R'P(O)(OH)O^-$ (wherein each R' is alkyl or aryl), $CH_3C(O)O^-$, acetylacetonate, $SO_4^{2-}$, $PF_4^-$, $PF_6^-$, $NO_2^-$, $NO_3^-$, $CH_3O^-$, $CH_2=CHCH_2^-$, $C_6H_5CN$, $CH_3CH=$, NO, $NH_3$, pyridine, $(C_2H_5)_3N$, mono-olefins, diolefins, triolefins, tetrahydrofuran, and the like. Of course, the active complex species is preferably free of any additional organic ligand or anion that might poison the catalyst and have an unacceptable adverse effect on the catalyst performance, such as possibly halogen atoms and sulfur atoms with a low degree of oxidation, such as mercaptanes, that may poison the catalyst.

Any amount of complex catalyst can be employed in the hydroformylation process, provided that the amount is sufficient to catalyze the desired hydroformylation reaction. In general, the concentration of complex catalyst provides for a concentration of Group 8-10 transition metal of greater than about 10 parts per million (ppm), preferably, greater than about 25 ppm, by weight calculated as free metal. Advantageously, the concentration of complex catalyst provides for a concentration of Group 8-10 transition metal of less than about 1,000 ppm, preferably, less than about 800 ppm, and more preferably, less than about 600 ppm, by weight calculated as free metal.

The olefinic reactants to be used in the hydroformylation process of this invention can be any terminally or internally olefinically-unsaturated aliphatic hydrocarbon, including straight chain, branched chain, and cyclic formulas. Such olefins contain preferably from 2 to about 60 carbon atoms and one or more unsaturated groups. Long-chain olefinically-unsaturated aliphatic hydrocarbons having from 10 to about 50 carbon atoms are preferred. Moreover, such olefins can contain substituents that essentially do not adversely interfere with the hydroformylation process, including, for example, carbonyl, carbonyloxy, hydroxy, oxycarbonyl, halo, alkyoxy, aryl, haloalkyl, cyano, and the like. Non-limiting examples of suitable olefinic unsaturated reactants include, for example, alpha olefins, internal olefins, alkyl alkenoates, alkenyl alkanoates, alkenyl alkyl ethers, alkenols, olefinically-unsaturated fatty acids, and olefinically-unsaturated fatty acid esters; the latter unsaturated fatty acid and ester species including naturally-occurring and genetically modified seed oils. A non-limiting list of suitable olefinically-unsaturated compounds includes ethylene, propylene, 1-butene, 1-pentene, 1-hexene, 1-octene, 1-decene, 1-dodecene, 1-octadecene, 2-butene, 2-methyl propene (isobutylene), isoamylene, 2-pentene, 2-hexene, 3-hexene, 2-heptene, cyclohexene, propylene dimers, propylene trimers, propylene tetramers, 2-ethylhexene, styrene, 3-phenyl-1-propene, butadiene, 1,3-cyclohexadiene, 1,4-cyclohexadiene, 1,7-octadiene, 3-cyclohexyl-1-butene, allyl alcohol, hex-1-en-4-ol, oct-1-ene-4-ol, vinyl acetate, allyl acetate, 3-butenyl acetate, vinyl propionate, 1-vinyl-3-cyclohexene, allyl propionate, allyl butyrate, methyl methacrylate, 3-butenyl acetate, vinyl ether, vinyl methyl ether, allyl ethyl ether, n-propyl-7-octenoate, methyl 1-decenoate, 3-butenenitrile, 5-hexenamide, methyl oleate, castor oil, soybean oil, canola oil, and sunflower oil, including high oleic variations of the aforementioned oils. Mixtures of any of the aforementioned olefinic starting materials can be employed, if desired. Preferably, the hydroformylation is useful for the production of aldehydes by the hydroformylation of alpha olefins containing from 2 to about 60 carbon atoms ($C_2$-$C_{60}$), or internal olefins containing from 6 to about 50 carbon atoms ($C_6$-$C_{50}$), and more preferably, from about 10 to about 50 carbon atoms ($C_{10}$-$C_{50}$) as found in unsaturated fatty acid and esters derived from seed oils.

The hydroformylation process of this invention is preferably conducted in the presence of an organic solvent for the Group 8-10 transition metal complex catalyst. Any suitable solvent that does not unduly interfere with the hydroformylation process can be used including those types of solvents commonly used in prior art carbonylation processes. By way of illustration, suitable solvents for rhodium-catalyzed hydroformylation processes include those disclosed, for example, in U.S. Pat. No. 3,527,809; U.S. Pat. No. 4,148,830; U.S. Pat. No. 5,180,854, and U.S. Pat. No. 5,929,289, the aforementioned citations being incorporated herein by reference. Non-limiting examples of suitable solvents include saturated hydrocarbons (e.g., pentane, octane, decane), aromatic hydrocarbons (e.g., benzene, toluene, xylene), ethers (e.g., tetrahydrofuran), nitriles (e.g., benzonitrile, acetonitrile, propionitrile), aldehydes (including higher boiling hydroformylation products and aldehyde liquid condensation products), ketones broadly including piperidones, pyrrolidones and pyrrolidinones (e.g., N-methylpyrrolidinone, N-methyl piperidone, 1,5-dimethyl-2-pyrrolidone, 2-hydroxyethyl pyrrolidone, N-cyclohexyl pyrrolidone), amides (e.g., dimethylformamide, dimethylacetamide, N-dimethylpropionamide), sulfoxides (e.g., dimethyl sulfoxide), sulfones (e.g., dimethyl sulfone, sulfolane), as well as ionic liquids and supercritical carbon dioxide. Mixtures of two or more solvents may also be employed. When the ligand employed is an ionic ligand, it is preferred to use a non-aqueous, aprotic, polar solvent selected from any in the list hereinabove, more preferably, N-methylpyrrolidinone (NMP). When the ligand employed is a non-ionic ligand, it is preferred to use a nonpolar solvent selected from any in the list hereinabove. The amount of solvent is not especially critical and need only be sufficient to provide the reaction medium with the desired amount of Group 8-10 transition metal concentration. Advantageously, the amount of solvent ranges from about 5 percent to about 95 percent by weight, based on the total weight of the reaction medium.

The hydroformylation process of this invention is preferably conducted in the presence of free ligand of Formula I, that is, ligand that is not complexed with the Group 8-10 transition metal. The free and complexed ligands can be identical species; or if desired, the free and complexed ligands can be different species falling within the scope of Formula I. While the carbonylation process of this invention can be carried out in any excess amount of free ligand, advantageously at least one mole of free ligand per mole of Group 8-10 transition metal is present in the reaction medium. For most purposes, preferably, the amount of ligand per mole of Group 8-10 transition metal is greater than about 1.1/1, more preferably, greater than about 1.3/1 is employed. Preferably, the amount of ligand per mole of Group 8-10 transition metal is less than about 100/1, more preferably, less than about 50/1. The aforementioned ratios correspond to the sum of both the free and complexed ligand. Make-up ligand can be added during the hydroformylation process at any time and in any suitable manner, so as to maintain a predetermined concentration of free ligand in the reaction medium.

The reaction conditions for effecting hydroformylation can be chosen from any of those conditions conventionally used and known for such processes. The total gas pressure of hydrogen, carbon monoxide, and olefinic unsaturated reactant in the hydroformylation process advantageously ranges from greater than about 1 psia (7 kPa) to less than about 10,000 psia (68,948 kPa). Preferably, the total pressure of hydrogen, carbon monoxide, and olefinic unsaturated reactant is advantageously less than about 2000 psia (13,790 kPa), and preferably, less than about 1500 psia (10,342 kPa). More specifically, the carbon monoxide partial pressure of the hydroformylation process of this invention is advantageously greater than about 1 psia (7 kPa), preferably, greater than about 3 psia (21 kPa). The carbon monoxide partial pressure of the hydroformylation process of this invention is advantageously less than about 1000 psia (6,8948 kPa), preferably, less than about 750 psia (5171 kPa). The hydrogen partial pressure is advantageously greater than about 5 psia (35 psia), preferably, greater than about 10 psia (69 kPa). The hydrogen partial pressure is advantageously less than about 1000 psia (6,8948 kPa), preferably, less than about 750 psia (5171 kPa). In general, the $H_2/CO$ molar ratio of gaseous hydrogen to carbon monoxide is advantageously greater than about 1/10, and preferably, equal to or greater than about 1/1. The $H_2/CO$ molar ratio is advantageously less than about 100/1, and preferably, equal to or less than about 10/1.

Further to the hydroformylation process of this invention, the reaction temperature will depend upon the particular olefinic reagent and metal catalyst employed, as well as the efficiency desired. Hydroformylation at reaction temperatures advantageously greater than about 30° C., and preferably, greater than about 40° C., are suitable. Hydroformylation at reaction temperatures advantageously less than about 150° C., and preferably, less than about 130° C. are suitable.

The hydroformylation process of this invention can be carried out in the liquid or gas phase, preferably, in one liquid phase, which can more preferably involve a continuous liquid phase recycle stream comprising the transition metal-ligand complex catalyst and any free ligand back to the hydroformylation reactor.

In the preferred hydroformylation process of this invention, the olefin conversion is advantageously greater than about 70 mole percent. For the purposes of this invention, "olefin conversion" is defined as the mole percentage of olefin feed converted to all products. Olefin conversion varies depending upon the specific olefin reactant, the specific form of the catalyst, and the specific process conditions employed. Preferably, the olefin conversion is greater than about 80 mole percent.

Likewise, in the preferred hydroformylation process of this invention, the selectivity to aldehyde product(s) is advantageously greater than about 60 mole percent. For the purposes of this invention, "selectivity" is defined as the mole percentage of aldehyde product produced, based on the moles of olefin converted. Again, the selectivity to aldehyde(s) varies based on the specific olefin reactant, the specific form of the catalyst, and the specific process conditions employed. Preferably, the selectivity to aldehyde is greater than about 70 mole percent, more preferably, greater than about 80 mole percent.

In the preferred process wherein the reactant olefin comprises one or more long-chain olefinically-unsaturated compounds, preferably, a mixture of unsaturated fatty acids or fatty acid esters, the effluent stream from the hydroformylation reactor can be treated with water so as to induce phase separation into a polar phase comprising water, non-aqueous organic solvent, e.g., N-methylpyrrolidinone, the transition metal-ligand complex catalyst, and optional free ligand, wherein the complexed and free ligands are ionically-charged ligands of Formula I, and a non-polar phase comprising one or more formyl-substituted products, preferably one or more formyl-substituted fatty acids or fatty acid esters, and non-polar solvent(s) as may be present. The polar phase is advantageously recycled back to the reactor, while the non-polar phase is worked up to recover purified aldehyde product(s) for downstream use. Representative art disclosing this separation method is found in U.S. Pat. No. 5,180,854 and WO 2004/096744, incorporated herein by reference.

The following examples are illustrative of the present invention and are not to be regarded as limiting thereof. Variations in operational parameters, such as reactants, process conditions, forms of the transition metal-ligand complex catalyst, and ligand species, all falling within the scope of the claims, will be apparent to those skilled in the art based on the description and examples contained herein. All of the parts, percentages, and proportions are given by mole percent, unless otherwise indicated.

Example 1

Preparation of Ligand 1 (with Reference to FIG. 1)

(a) Preparation of 3-(Dicyclohexylphosphino)cyclohexanone

Dicyclohexylphosphine (29.74 g; 0.15 moL) is added to a 250 mL single neck glass Schlenk flask with magnetic stirring bar in the dry nitrogen glove box. All glassware is pre-dried at 150° C. for more than 48 h. A glass spiral condenser cooled with a fan is added to the Schlenk flask. Heating of the magnetically stirred dicyclohexylphosphine commences to 60° C., followed by addition of 2-cyclohexen-1-one (16.98 g; 0.177 moL) in 9 closely equivalent aliquots over 50 min. After addition of the final aliquot, the temperature is increased to 90° C. and held for 16.5 h. The condenser is replaced with a ground glass stopper and vacuum introduced via the inlet of the Schlenk flask. Distillation of clear liquid from the reactor into a liquid nitrogen trap is conducted at 190-197° C. and 0.15 to 0.10 mm Hg (20.0 to 13.3 Pa). The product remaining after the vacuum distillation is cooled to provide 27.73 g of white crystalline solid 3-(dicyclohexylphosphino)-cyclohexanone (62.8% yield based on dicyclohexylphosphine). Gas chromatographic (GC) analysis demonstrated >96 area % purity. $^{31}$P NMR (CH$_3$OD, ppm): 8.81 (major) and 8.17 (minor). $^1$H NMR (CD$_3$OD, ppm): 1.0-2.4 (m, 31H, cyclohexyls).

(b) Preparation of 3-(Dicyclohexylphosphino)Cyclohexanol Borane 3-(Dicyclohexyl-phosphino)cyclohexanone (7.36 g; 25.0 mmoL) and anhydrous, deoxygenated tetrahydrofuran (25 mL) are added to a 500 mL single neck glass Schlenk flask with magnetic stiffing bar in the dry nitrogen glove box. All glassware is pre-dried at 150° C. for more than 48 h. The tetrahydrofuran is chromatographically purified in a glove box over activated alumina prior to use. The sealed Schlenk flask is removed from the glove box and placed on a Schlenk line under dynamic nitrogen flow. A side-arm vented glass addition funnel is charged in the glove box with 1.0 M borane-tetrahydrofuran (58.3 mL; 58.3 mmoL). The outlet end of the addition funnel is sealed with a ground glass cap and a Schlenk adaptor is placed on the inlet. The sealed addition funnel is removed from the glove box and placed on a Schlenk line under dynamic nitrogen flow. The Schlenk flask and addition funnel are coupled and then maintained under dynamic nitrogen flow. A sodium chloride-ice bath is placed under the Schlenk flask and magnetic stiffing commenced. Dropwise addition of borane-tetrahydrofuran is completed over 2.4 h. The reaction is stirred for the next 16 h in the thawing NaCl-ice bath. The Schlenk flask is sealed and reintroduced into the glovebox. After placement of a spiral condenser cooled with a fan on the Schlenk flask, the magnetically stirred reactor is heated to 50° C. and held for 24 h. After cooling to 23° C., deoxygenated water (25 mL) is added dropwise, allowing gas bubbles to subside between drop additions. The solution is added to a separatory funnel and extracted with deoxygenated diethyl ether (25 mL). The diethyl ether extract is washed with deoxygenated 1N hydrochloric acid (25 mL) then deoxygenated deionized water (25 mL). The extract is dried over magnesium sulfate, then passed through a medium-fritted glass funnel.

The filtrate is collected into a clean Schlenk flask and diethyl ether vacuum distilled from the product. Drying on the vacuum line for 16 h at 75° C. to 0.02 mm Hg provided 7.03 g of white crystalline solid 3-(dicyclohexylphosphino) cyclohexanol borane (90.6% yield based on dicyclohexylphosphine). $^{31}$P NMR (CH$_3$OD, ppm): 25.92 and 26.75. $^1$H NMR (CD$_3$OD, ppm): 0.93-0.6 (broad m, 3H, BH$_3$), 1.02-1.95 (m, 31H, cyclohexyls), 2.05 (broad d, 1H, cyclohexyl H adjacent to cyclohexyl —OH), 3.36 broad s, 1H, —OH).

(c) Preparation of sodium 4-[3-(dicyclohexylphosphino)cyclohexyloxy]butane-1-sulfonate borane Sodium hydride (95% dry) (0.725 g; 30.21 mmoL) and anhydrous, deoxygenated dimethylsulfoxide (25 mL) are added to a 500 mL single-neck glass Schlenk flask with magnetic stiffing bar in a dry nitrogen glove box. All glassware used is pre-dried at 150° C. for more than 48 h. A side-arm vented glass addition funnel was charged in the glovebox with 3-(dicyclohexylphosphino)cyclohexanol borane (7.03 g; 22.66 mmoL) dissolved in anhydrous, deoxygenated dimethylsulfoxide (50 mL). A spiral condenser cooled with a fan was placed on the inlet of the addition funnel. Dropwise addition of 3-(dicyclohexyl-phosphino)cyclohexanol borane solution into the magnetically stirred slurry of sodium hydride in dimethylsulfoxide and is completed over 3.3 h. The reaction is stirred for the next 17 h at the 23° C. temperature in the glovebox. The addition funnel/ spiral condenser assembly is removed from the Schlenk flask; then 1,4-butanesultone (5.14 g; 37.75 mmoL) is added in a single addition followed by replacement of the spiral condenser on the Schlenk flask. An exotherm from 23° C. to 27.2° C. is observed. Four minutes after the exothermic maximum, heating of the magnetically stirred mixture commences to 85° C. to give a light yellow colored solution. After 7.9 h at 85° C. the condenser is replaced with a ground glass stopper and vacuum introduced via the inlet of the Schlenk flask. Distillation of volatiles from the Schlenk flask leaves behind 5.61 g of white powder. Addition of the white powder to magnetically stirred, deoxygenated, boiling, reagent ethanol (950 mL) provides a slightly hazy mixture which is vacuum filtered through a medium fritted glass funnel while still at boiling. The amber colored solid (less than 0.5 g) left on the filter is discarded. The filtrate is concentrated by vacuum distillation to a 300 mL solution. After standing in the glovebox at 23° C. a fine, crystalline, white slurry is obtained. The white powder recovered by vacuum filtration on a medium fritted glass funnel is washed in situ with deoxygenated reagent ethanol (25 mL), then sealed into a clean Schlenk flask and dried to a constant weight on the glove box vacuum line. The product, 3.38 g (33.4% yield), is a white crystalline solid sodium 4-[3-(dicyclohexylphosphino)cyclohexyloxy] butane-1-sulfonate borane. $^{31}$P NMR (CH$_3$OD, ppm): 26.21 and 26.97. Negative Ion Electrospray Mass Spectroscopy (MS) confirms an isotopic cluster for the anion of C$_{22}$H$_{43}$PSO$_4$B at m/z 445 (M-Na$^+$).

(d) Preparation of sodium 4-[3-(dicyclohexylphosphino)cyclohexyloxy]butane-1-sulfonate The boron-protected ligand (2.0 g; 4.27 mmol) is placed in a 100 mL three-neck flask in a nitrogen purge box. Then, 25 mL of morpholine (Sure Seal, redistilled grade) is added; the system is purged with nitrogen and heated with stiffing at 110° C. for 2 h. The mixture is left overnight at room temperature with stirring. The white solid is filtered off, washed with deoxygenated acetone (10 mL×2) and dried to give 1.29 g of the crude ligand. This material is dissolved at stirring in dilute sulfuric acid prepared from 2 mL of 96 wt % sulfuric acid and 50 mL of water. The acid solution is extracted with methylene chloride (10 ml×6). The organic phases are separated and combined; methylene chloride is evaporated and the residue is dried in vacuum at 1 mm Hg for 1 h to give 0.22 g of 4-[3-(dicyclohexylphosphino)-cyclohexyloxy]butane-1-sulfonate. This intermediate is dissolved in 2 ml of deoxygenated methanol containing 20 mg of sodium hydroxide. Methanol is evaporated, and the residue is dried in vacuum at 1 mm Hg for 2 h to give 0.23 g (12%) of white powder sodium 4-[3-(dicyclohexylphosphino)cyclohexyloxy]butane-1-sulfonate. $^{31}$P NMR (CH$_3$OD, ppm): 13.21 (major) and 12.45 (minor).

Example 2

Ligand 1 Testing with Soy Methyl Ester at L/Rh=10/1

In this example Ligand 1, sodium 4-[3-(dicyclohexylphosphino)cyclohexyl-oxy]butane-1-sulfonate prepared as in Example 1 hereinabove, is tested in the hydroformylation of a mixture of methyl esters of mono-, di-, and tri-unsaturated fatty acid esters derived from soy oil. The ligand is provided as a 0.05 M solution in N-methyl-2-pyrrolidinone (NMP). Rhodium (I) dicarbonyl acetylacetonate is provided to the reaction as a 0.05 M solution in NMP. The ligand solution (2.268 ml) is mixed with rhodium (I) dicarbonyl acetylacetonate (0.228 ml) and the soy methyl esters (1.50 ml) in a pressure reactor under a nitrogen atmosphere. The ligand (L)/Rh molar ratio is 10/1; the Rh concentration is 300 parts per million (ppm). The reactor is sealed, pressurized, and heated to 75° C. Hydroformylation is performed at 400 psi (2758 kPa) at a gas ratio CO/$H_2$ of 1:1, then stopped after 3 h. The mixture is analyzed by GC with the results shown in Table 1.

TABLE 1

| [1] Hydroformylation of Soy Methyl Esters | | | |
|---|---|---|---|
| | Example | | |
| | CE-1 | Ex. 2 | Ex. 3 |
| Ligand (L) | DCHPPMS | Ligand 1 | Ligand 1 |
| (L/Rh mole ratio) | (10/1) | (10/1) | (5/1) |
| Olefin Conversion (mole %) | 91 | 78 | 85 |
| Aldehyde selectivity (mole %) | 87 | 72 | 80 |

[1][Rh] = 300 parts per million (ppm); 75° C.; 400 psi (2758 kPa); CO/$H_2$ = 1:1; 3 h.
2. DCHPPMS = dicyclohexylphenylphosphine monosulfonate sodium salt.

Example 3

Testing Sulfonated Ligand 1 with Soy Methyl Esters at L/Rh=5/1

Ligand 1A is evaluated in the hydroformylation of soy methyl esters in the manner described in Example 2, with the exception that the L/Rh molar ratio is only 5/1. Results are shown in Table 1.

Comparative Experiment 1

Example 2 is repeated with the exception that a ligand of the prior art, specifically, sodium dicyclohexylphosphinobenzene sulfonate, DCHPPMS, is used in place of Ligand 1.

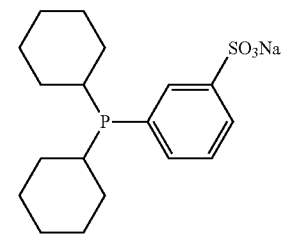

sodium 3-(dicyclohexylphosphino)benzene sulfonate

Results are shown in Table 1. When comparative experiment CE-1 is compared with Examples 1 and 2, it is seen that the ionic ligand of the present invention, having all three phosphorus alkyl bonds, is somewhat less active toward soy oil hydroformylation and somewhat less selective to aldehyde products, as compared with the prior art ligand having a phosphorus-aryl bond. Nevertheless, the ligand of the invention is considerably more stable over a longer time on stream, because it comprises no aryl-phosphorus bond and therefore cannot participate in alkyl-aryl exchange. In contrast, the ligand of the prior art comprises an alkyl-aryl bond, and thus is prone to significant alkyl-aryl exchange.

What is claimed is:

1. A composition comprising a class of sulfonated triorganophosphine compounds represented by the following formula:

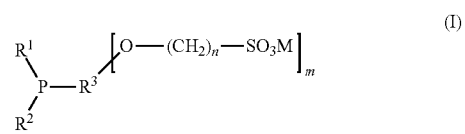

wherein R1 and R2 each individually represent a monovalent hydrocarbyl or substituted hydrocarbyl radical selected from alkyl, aralkyl, and alicyclic radicals; wherein R3 represents a divalent or polyvalent alkylene or alicyclic radical which is bonded to the phosphorus atom and to one or more sulfonate substituents via an alkylether link, and further wherein R3 does not contain any aryl moieties; n is an integer representing a number of methylene groups in the alkylether link ranging from 1 to about 5; M represents a monovalent cation; and m is an integer ranging from 1 to 3 representing a total number of sulfonated alkylether substituents bonded to R3; and wherein in each of R1, R2, and R3 the carbon atom attached to the phosphorus atom or a carbon atom directly bonded to the carbon atom attached to the phosphorus atom is additionally bonded to 2 other carbon atoms and 1 hydrogen atom.

2. The composition of claim 1 wherein R1 and R2 are each individually selected from alkyl radicals containing from 3 to 12 carbon atoms, aralkyl radicals containing from 6 to 12 carbon atoms, and alicyclic radicals containing from 3 to 10 carbon atoms.

3. The composition of claim 1 wherein R1 and R2 are each individually selected from iso-propyl, iso-butyl, sec-butyl, 2,2-dimethylpropyl, 2-methylbutyl, 1,1-dimethylpropyl, 2-ethylhexyl, benzyl, 2-methylbenzyl, 2,6-dimethylbenzyl, 1-phenylethyl, phenylcyclohexyl, 1,2,3,4-tetrahydronaphthyl, phenylcyclopentyl, cyclopentyl, cyclohexyl, cycloheptyl, cyclooctyl, ethylcyclohexyl, norbornyl, adamantyl, and dicyclopentyl.

4. The composition of claim 1 wherein R1 and R2 are substituted with one or more substituents selected from cyano, fluoro, trifluoromethyl, trialkylsilyl, alkoxy, carboalkoxy (ester), dialkylamino, and dialkylamido.

5. The composition of claim 1 wherein R3 is selected from divalent alkylene radicals having greater than 3 and less than 10 carbon atoms, and is optionally substituted with one or more substituents selected from fluoride, alkoxy, cyano, and/or alkyl groups.

6. A complex catalyst or complex catalyst precursor composition comprising a Group 8-10 transition metal bonded to at least one ligand represented by the composition of claim 1, the transition metal optionally being further bonded to carbon monoxide, hydrogen, or both carbon monoxide and hydrogen.

7. The complex catalyst of claim 6 wherein the transition metal is selected from ruthenium, rhodium, cobalt, and iridium.

8. The composition of claim 1 wherein —ORb3 is selected from the following species:

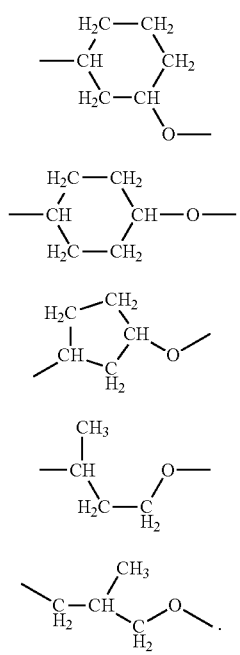

9. A hydroformylation process comprising contacting one or more olefinically-unsaturated compounds with carbon monoxide and hydrogen in the presence of a transition metal-ligand complex catalyst, and optionally free ligand, wherein the ligand is represented by the composition of claim 1, the contacting being conducted under process conditions sufficient to prepare one or more corresponding aldehyde products.

10. The process of claim 9 wherein the olefin is selected from olefinically-unsaturated aliphatic hydrocarbons having from 10 to 50 carbon atoms.

11. The process of claim 9 wherein the olefin is selected from the group consisting of alpha olefins, internal olefins, alkyl alkenoates, alkenyl alkanoates, alkenyl alkyl ethers, alkenols, olefinically-unsaturated fatty acids, and olefinically-unsaturated fatty acid esters.

12. The process of claim 9 wherein the Group 8-10 transition metal is present in a concentration greater than 0 parts per million (ppm) and less than 1,000 ppm by weight, calculated as free metal.

13. The process of claim 9 wherein temperature is greater than 30° C. and less than 150° C.

14. The process of claim 9 wherein the total gas pressure of hydrogen, carbon monoxide, and olefinic unsaturated reactant in the hydroformylation process ranges from greater than 1 psia (7 kPa) to less than 10,000 psia (68,948 kPa).

15. The process of claim 9 wherein partial pressure of carbon monoxide is greater than 1 psia (7 kPa) and less than 1000 psia (6,8948 kPa), and wherein partial pressure of hydrogen is greater than 5 psia (35 psia) and less than 1000 psia (6,8948 kPa).

16. The process of claim 9 wherein a molar ratio H2/CO of gaseous hydrogen to carbon monoxide is greater than 1/10 and less than 100/1.

17. The process of claim 9 wherein the transition metal is selected from ruthenium, rhodium, cobalt, and iridium.

18. A complex catalyst solution or complex catalyst precursor solution comprising a solvent, a complex catalyst or catalyst precursor composition comprising a Group 8-10 transition metal bonded to at least one ligand, the solution optionally further comprising free ligand; wherein the bonded and free ligands are represented by the composition of claims 1 to 5 and 8; and wherein optionally the Group 8-10 transition metal is bonded to carbon monoxide, hydrogen, or both carbon monoxide and hydrogen.

19. The composition of claim 1 wherein the sulfonated triorganophosphine compounds are selected from the group consisting of compounds of the following formula:

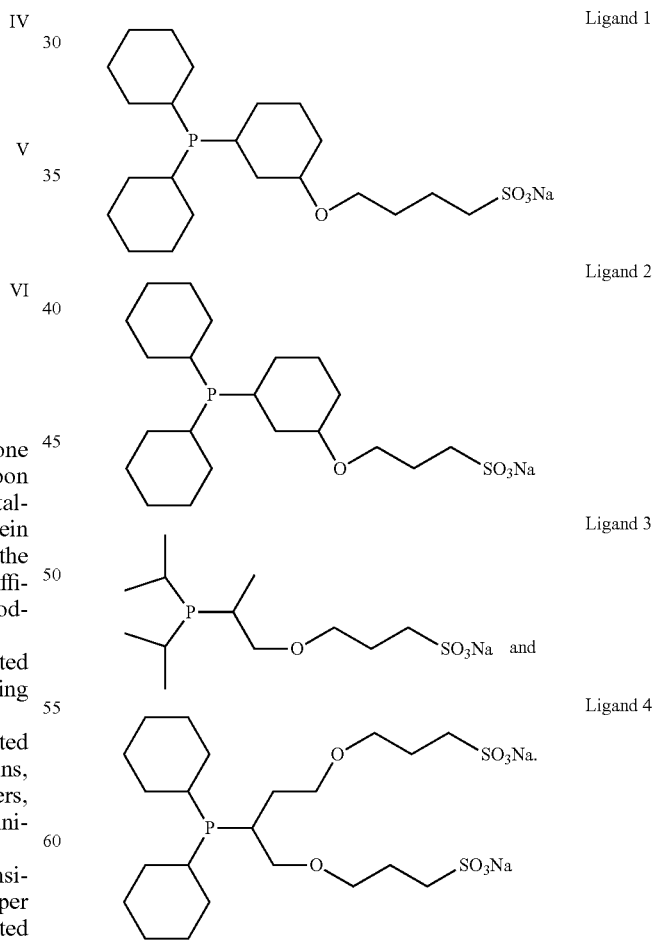

* * * * *